United States Patent
Ganne

(12) 
(10) Patent No.: US 6,251,407 B1
(45) Date of Patent: Jun. 26, 2001

(54) THERAPEUTIC COMPOSITION COMPRISING AN ANTIGEN OR AN IN VIVO GENERATOR OF A COMPOUND COMPRISING AN AMINO ACID SEQUENCE

(75) Inventor: Vincent Ganne, La Varenne Saint Hillaire (FR)

(73) Assignee: Societe d'Exploitation de Produits pour les Industries Chimque (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/820,943

(22) Filed: Jun. 6, 1997

Related U.S. Application Data

(62) Division of application No. 08/478,091, filed on Jun. 7, 1995.

(30) Foreign Application Priority Data

Apr. 20, 1995 (FR) .................................................. 95 04739

(51) Int. Cl.$^7$ .................................................. A61K 47/12
(52) U.S. Cl. ...................................... 424/278.1; 424/283.1
(58) Field of Search ............................. 424/278.1, 280.1, 424/283.1, 614, 639, 677; 514/23, 937, 938

(56) References Cited

U.S. PATENT DOCUMENTS

| | | | |
|---|---|---|---|
| 3,925,544 | * 12/1975 | Shechmeister et al. | 424/89 |
| 4,073,743 | * 2/1978 | Midler et al. | 252/309 |
| 4,235,771 | 11/1980 | Adam et al. . | |
| 4,411,894 | * 10/1983 | Schrank et al. | 424/189 |
| 4,673,666 | * 6/1987 | Hettche et al. | 514/23 |
| 4,696,921 | * 9/1987 | Merkli et al. | 514/157 |
| 4,720,386 | * 1/1988 | McCollester et al. | 424/88 |
| 4,806,350 | * 2/1989 | Gerger | 424/88 |
| 4,877,611 | * 10/1989 | Cantrell | 424/88 |
| 4,976,954 | 12/1990 | Kleber et al. . | |
| 5,080,903 | 1/1992 | Ayache et al. . | |
| 5,393,791 | * 2/1995 | Roberts | 514/762 |
| 5,422,109 | * 6/1995 | Brancq et al. | 424/184.1 |
| 5,444,041 | * 8/1995 | Owen et al. | 514/2 |
| 5,656,465 | 8/1997 | Panicali et al. . | |
| 5,690,942 | 11/1997 | Hjorth . | |

FOREIGN PATENT DOCUMENTS

| | | |
|---|---|---|
| 224 260 | 6/1987 | (EP) . |
| 2 672 495 | 8/1992 | (FR) . |
| 2 674 755 | 10/1992 | (FR) . |

OTHER PUBLICATIONS

Eliot Marshall & James Wilson Science 269: 1050–1055, Aug. 1995.*
Rosoff, "Specialized Pharmaceutical Emulsions", In: Pharmaceutical Dosage Forms, Disperse Systems, vol. 1, Lieberman et al. eds., Marcel Dekker, Inc., New York, 1988, pp. 245–283, 1988.*
Chemical Abstracts, vol. 105, No. 23, Dec. 8, 1986, Abstract No. 202906.
Wassef et al., "Liposomes as Carriers for Vaccines", Immunomethods 4, 217–222 (1994).
Gould–Fogerite et al., "Lipid Matrix–Based Subunit Vaccines: A Structure–Function Approach to Oral and Parenteral Immunization", AIDS Res. Human Retrovir. 10, Suppl. 2, S99–S103 (1994).
Warren et al., "Current Status of Immunological Adjuvants", Ann. Rev. Immunol. 4, 389–417 (1986).
Kimura et al., CA Accession No. 110:82524, Abstract, JP 63215635, "Storage–stable calcium gluconate–containing creams for treatment of burns caused by hydrofluoric acid".
Pertsev et al., CA Accession No. 102:32068, Abstract, Khim–Farm. Zh. (1984), 18(9), 1110–13, "Dependence of the antimicrobial activity of chemical preservatives in suspensions on several pharmaceutical factors".
Belokrylov et al. Biulleten Eksperimentalnoi Biologii I Meditsiny 102(7):51–3 Abstract.

* cited by examiner

*Primary Examiner*—Donna C. Wortman
(74) *Attorney, Agent, or Firm*—Hunton and Williams

(57) ABSTRACT

A therapeutic composition comprising (i) at least one antigen or at least one in vivo generator of a compound comprising an amino acid sequence and (ii) at least one adjuvant comprising at least one pharmaceutically acceptable and water-soluble salt of an organic anion and a metal cation.

8 Claims, No Drawings

THERAPEUTIC COMPOSITION COMPRISING AN ANTIGEN OR AN IN VIVO GENERATOR OF A COMPOUND COMPRISING AN AMINO ACID SEQUENCE

This application is a divisional of application Ser. No. 08/478,091, filed Jun. 7, 1995.

BACKGROUND OF THE INVENTION (i) Field of the Invention

The present invention relates to a therapeutic composition comprising at least one antigen, in particular an antigen of viral, bacterial or parasitic origin, or at least one in vivo generator of a compound comprising an amino acid sequence, and at least one adjuvant.

(ii) Description of Related Art

The use of adjuvants in therapeutic compositions of the vaccine type has been known for a long time. The main objective of these adjuvants is to allow an increase in the immune response. These adjuvants are diverse in nature. They may, for example, consist of liposomes, oily phases, for example the Freund type of adjuvants, generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide (Al(OH)$_3$) is the most commonly used adjuvant. These adjuvants are described in particular in the article by Rajesh K. Gupta et al "Adjuvants, balance between toxicity and adjuvanticity", Vaccine, Vol. 11, issue 3, 1993, pages 993–306.

The adjuvants mentioned above have the drawback of limited efficiency. Moreover, they may induce a certain toxicity with regard to individuals treated. More particularly, when these therapeutic compositions are injected, the formation of lesions and other local reactions such as granulomae is observed at the point of injection. These drawbacks are less pronounced when the adjuvant is aluminum hydroxide. Accordingly, the latter compound is one of the most commonly used adjuvants. Recently, however, aluminum hydroxide, like all aluminum-based compounds, has come to be suspected of being a factor promoting the appearance of certain diseases, such as renal dysfunctions or Alzheimer's disease. In addition, it is known that aluminum hydroxide efficiently induces only humoral immunity and not cell immunity.

SUMMARY AND OBJECTS OF THE INVENTION

A first object of the invention is to provide therapeutic compositions comprising an adjuvant which allows an increase in the immune response which is at least equal to that imparted by aluminum hydroxide, without causing lesions or local reactions of the granuloma type and which is not liable to promote the appearance of diseases in the individual treated.

Another object of the invention is to provide a therapeutic composition comprising an adjuvant which efficiently induces both cell immunity and humoral immunity.

Yet another object of the invention is to provide a method for making a therapeutic composition using the adjuvant of the invention.

In a first aspect, the present invention relates to a therapeutic composition comprising (i) at least one antigen or at least one in vivo generator of a compound comprising an amino acid sequence and (ii) at least one adjuvant comprising at least one pharmaceutically acceptable and water-soluble salt of an organic anion and a metal cation.

In a second aspect, the present invention relates to a method of making a composition intended for the prevention or treatment of infectious diseases comprising combining (a) at least one adjuvant comprising at least one pharmaceutically acceptable and water-soluble salt of an organic anion and a metal cation and (b) at least one antigen or at least one in vivo generator of a compound comprising an amino acid sequence.

In a third aspect, the present invention relates to a method for treating a functional disease comprising administering to a patient the therapeutic composition as described above.

In another aspect, the invention relates to an adjuvant composition comprising a pharmaceutically acceptable and water-soluble salt and (a) an oily adjuvant, (b) a surfactant and/or (c) an oily adjuvant combined with a surfactant.

With the foregoing as well as other objects advantages and features of the invention that will become hereinafter apparent, the nature of the invention may be better understood by reference to the following detailed description of the preferred embodiments and to the appended claims.

DETAILED DESCRIPTION OF PREFERRED EMBODIMENTS

In the sense of the present invention, a water-soluble salt may be such that its solubility in water is greater than or equal to 10 g/l, preferably between 10 and 2000 g/l.

The metal cation constituting said pharmaceutically acceptable salt is preferably a divalent cation. This cation is advantageously a cation of a metal chosen from the group consisting of manganese, calcium and zinc. Manganese is a very particularly preferred metal within the context of the present invention. The reason for this is that it has been observed that pharmaceutically acceptable and water-soluble salts according to the invention comprising an Mn$^{2+}$ cation allow the induction of a particularly large immune response, while at the same time being low in toxicity.

The organic anion constituting said pharmaceutically acceptable salt is advantageously an anion of a compound comprising at least one oxygenated functional group, preferably a phosphoric group —PO$_4$H$_2$, or a carboxylic group —COOH.

Glycerophosphoric acid is a preferred anion containing a phosphoric group.

The preferred anions comprising at least one carboxylic group are derived from compounds chosen from:

acid saccharides, preferably acid saccharides having from 5 to 7 carbon atoms, more preferably those having 6 or 7 carbon atoms, mono- or polycarboxylic acids, amino acids.

The preferred mono- or polycarboxylic acids are fumaric acid and the compounds of the formula (I):

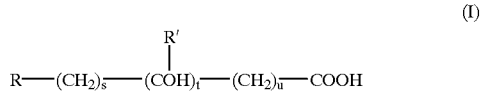

(I)

where:

R represents COOH, $CH_3CO$, $CH_3$ or $CH_2OH$,

R' represents H or COOH and s, t and u, which may be identical or different, are between 0 and 3.

Preferred compounds of formula (I) are acetic acid, lactic acid, tartaric acid, malic acid, citric acid and pyruvic acid.

In the sense of the present invention, an acid saccharide is of a saccharide comprising at least one carboxylic function, a saccharide being a glucide consisting of reducing sugars. These acid saccharides are advantageously aldose derivatives obtained by oxidation of the primary alcohol function or of the aldehyde function into a carboxylic function. Such compounds may most particularly include of gluconic acid, glucuronic acid, fructoheptonic acid, gluconoheptonic acid and glucoheptonic acid. When the organic anion is derived from an amino acid. this amino acid may be an α-amino acid such as glutamic acid, methionine and, most particularly, aspartic acid.

A pharmaceutically acceptable, water-soluble salt according to the invention may comprise a polyvalent cation, especially a divalent cation, combined with an organic anion or with several organic anions of different nature. Thus, by way of example, a divalent cation such as the calcium cation may be combined with an anion derived from gluconoheptonic acid and an anion derived from gluconic acid.

A water-soluble adjuvant most particularly preferred within the context of the present invention consists of manganese gluconate.

A therapeutic composition according to the present invention may comprise between 0.01 and 1000 mg/ml, preferably between 0.1 and 150 mg/ml, of an adjuvant as defined above.

A therapeutic composition according to the invention may be prepared by simple mixing of an aqueous suspension containing the antigen or said in vivo generator with an aqueous solution of the salt defined above.

Besides the adjuvant comprising a pharmaceutically acceptable and water-soluble salt as defined above, the therapeutic composition according to the invention may also comprise an oily adjuvant. In such a case, the therapeutic composition according to the invention is advantageously in the form of an emulsion combining at least one aqueous phase and at least one oily phase.

This emulsion may be of the water-in-oil (W/O) type or, preferably, of the oil-in-water (O/W), water-in-oil-in-water (W/O/W) or microemulsion type. Such an emulsion may be prepared according to the standard methods for the preparation of an emulsion, in particular according to the processes described in patent applications EP-A-489,181 and EP-A-481,982. Thus, the oil constituting the oily phase may be emulsified, with stirring, with the aqueous phase including an aqueous solution or suspension containing the antigen.

An emulsion according to the invention may contain, by weight, from 0.5% to 99.5% of oily phase per 99.5% to 0.5% of aqueous phase, preferably from 5% to 95% of oily phase per 95 to 5% of aqueous phase and, more preferably, from 25 to 27% of oily phase per 75 to 25% of aqueous phase. The emulsion must be stable preferably for at least 12 months when it is stored at 4° C.

The oily adjuvant may be a mineral oil, a non-mineral oil or a mixture of a mineral oil and a non-mineral oil. Said mineral oils may be natural or synthetic. Said non-mineral oils may be of plant, animal or synthetic origin. The non-mineral oils are advantageously metabolizable. All these oils are devoid of toxic effects with regard to the host organism into which the composition of the invention is administered. They are preferably liquid at the storage temperature (about +4° C.) or at least make it possible to give emulsions which are liquid at this temperature. An advantageous mineral oil according to the invention may include an oil comprising a linear carbon chain having a number of carbon atoms preferably greater than 16, and free of aromatic compounds. Such oils may, for example, be those marketed under the name "MARCOL 52" (produced by Esso France) or "DRAKEOL 6VR" (produced by Penreco USA).

Examples of synthetic non-mineral oils which may be mentioned are polyisobutenes, polyisopropenes, esters of alcohols and fatty acids, such as, for example, ethyl oleate and isopropyl myristate, mono-, di- or triglycerides, propylene glycol esters, partial glycerides such as corn oil glycerides, for instance those marketed by the company SEPPIC under the name LANOL TM, maisin and oleyl oleate. Among the plant oils which may be mentioned are unsaturated oils rich in oleic acid which are biodegradable, for example groundnut oil, olive oil, sesame oil, soya oil or wheatgerm oil.

The animal oils may include in particular squalene, squalane or spermaceti oil.

Moreover, when it is in the form of an emulsion as defined above, the therapeutic composition according to the invention may also advantageously contain one or more surface-active agents. The latter agent has a lipophilic or hydrophilic nature characterized by an HLB (hydrophilic-lipophilic balance) value between 1 and 19.

Such a surfactant may include:

an alkylpolyglycoside or a mixture of alkyl-polyglycosides of formula Ra—(O)—Zn where Ra represents a linear or branched saturated aliphatic radical comprising from 4 to 24 carbon atoms, preferably from 8 to 22 carbon atoms, Z is a sugar residue, preferably glucose, and n is between 1 and 5, preferably between 1.1 and 2, saponins, lecithins, polyoxyethylated alkanols such as those marketed under the name BRIJ by the company ICI, polymers comprising polyoxyethylene and polyoxypropylene blocks, such as those marketed under the name PLURONIC by the company BASF.

Particularly preferred surfactants are polyethylene glycol esters obtained by condensation of a fatty acid, in particular a fatty acid which is liquid at 20° C., with a polyethylene glycol of molecular weight between 80 and 2000; such a surfactant is marketed by the company SEPPIC under the tradename SIMULSOL 2599.

Another surface-active agent preferred within the context of the present invention is an ester obtained by condensation of a fatty acid, advantageously a fatty acid which is liquid at 20° C., with a sugar, sorbitol, glycerol or a polyglycerol, preferably a polyglycerol comprising from 2 to 5 glycerol units. Said sugar may be glucose, sucrose or, preferably, mannitol. By way of particularly preferred mannitol ester, there may be mentioned mannitol oleates obtained by dehydration of the polyhydroxylated carbon chain of mannitol which undergoes 1–4 or 2–6 cyclization.

Derivatives of these sugar esters, of polyethylene glycol, of sorbitol, of glycerol or of polyglycerol may also be used. These derivatives have a hydrophilicity which is modified in particular by grafting hydrophilic functions such as alcohol, polyol, ethylene oxide, propylene oxide, carboxylic acid, amine or amide. Such derivatives may, for example, include polyoxyethylated fatty esters of sorbitan, such as the TWEENs (conf. International Cosmetic Ingredient Dictionary, 5th ed. 1993).

Another preferred type of surfactant is ethoxylated plant oils such as, for example, ethoxylated castor oil, this oil being optionally hydrogenated.

A surface-active agent according to the invention is preferably pharmaceutically acceptable for an injectable use; it must in particular be free of heavy metals and have very low acid numbers or peroxide numbers. It is also desirable for it to satisfy the harmlessness test standards such as, for example, those described by S. S. Berlin, Annals of Allergy, 1962, 20, 473 or the tests of abnormal toxicity described in the European Pharmacopoeia. The surface-active agent is preferably combined with the oily adjuvant before formation of the emulsion.

The concentration of surface-active agent in the therapeutic composition may be between 0.01 and 500 mg/ml, preferably between 0.1 and 200 mg/ml.

Oils associated with a surface-active agent (mannitol ester) which are most particularly suitable within the context of the present invention are those marketed by the company SEPPIC under the tradename "MONTANIDE". The nature of these oils, the type of emulsion which can be obtained with them and the properties (viscosity and conductivity) of these emulsions are featured in Table 1 below:

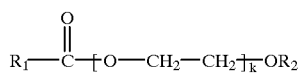

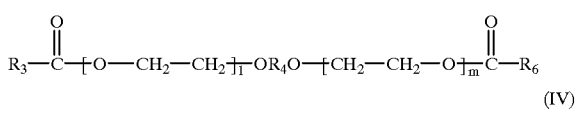

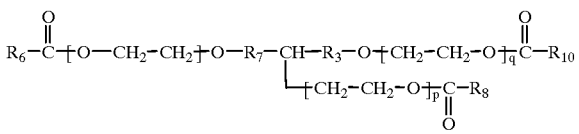

in which:

$R_1$, $R_3$, $R_5$, $R_6$, $R_8$ and $R_{10}$ represent a saturated or unsaturated, linear or branched hydrocarbon chain having from 5 to 30 carbon atoms;

$R_2$, $R_4$, $R_7$, and $R_9$ represent a saturated, or unsaturated, linear or branched hydrocarbon chain having from 1 to 5 carbon atoms;

TABLE 1

| No. | Commercial name | Oil/ manitol esters | Type of emulsion | Aqueous phase/ emulsion (% by weight) | Viscosity (mPa s) | Conductivity at 25° C. ($\mu$S cm$^{-1}$) |
|---|---|---|---|---|---|---|
| 1 | MONTANIDE ISA 25 | Mineral | O/W | 75% | 20 | 5000 |
| 2 | MONTANIDE ISA 25A | Mineral + avridine | O/W | 75% | 20 | 5000 |
| 3 | MONTANIDE ISA 28 | Mineral + ethyloleate | O/W | 75% | 25 | 1000 |
| 4 | MONTANIDE ISA 206 | Mineral | W/O/W | 50% | 50 | 1000 |
| 5 | MONTANIDE ISA 50 | Mineral | W/O | 50% | 200 | 1 |
| 6 | MONTANIDE ISA 708 | Plant | W/O | 30% | 70 | 1 |

*Avridine = N,N-dioctadecyl-N',N'-bis(2-hydroxyethyl)-propanediamine.

The oily adjuvant may also include a self-emulsifiable oil, that is to say an oily preparation capable of forming a stable emulsion with an aqueous phase, with virtually no energy input, for example by dispersion in the aqueous phase by slow mechanical stirring. In this respect, self-emulsifiable oils such as those known in the European Pharmacopoeia under the names Labrafil and Simulsol may be mentioned. These oils are polyglycolyzed glycerides.

Preferred self-emulsifiable oils are those described in French patent application No. 9500497 filed on Jan. 18, 1995, in the name of the Applicant, entitled "Utilisation d'esters d'acides gras éthoxylés comme composants auto-émulsionnables notamment utiles pour la préparation de compositions phytosanitaires ou de médicaments à usage vétérinaire ou humain" [Use of ethoxylated fatty acid esters as self-emulsifiable components which are particularly useful for the preparation of plant-protection compositions or medicinal products for human or veterinary use]. These oils include ethoxylated fatty acid esters corresponding to one of the following formulae:

the total number of ethylene oxide molecules represented in the abovementioned formulae II, III and IV by k, 1+m and n+p+q, respectively, being an integer such that the HLB value of said compounds is between about 4 and about 10, preferably between about 5 and about 9.

$R_1$ is preferably chosen from palmitic, stearic, ricinoleic, oleic, linoleic and linolenic acid residues, $R_2$ represents a methyl radical and k is an integer between 1 and 5, preferably equal to 2, and moreover the preferred ethoxylated fatty acid esters of formula III are those in which:

(i)—$R_6$, $R_8$ and $R_{10}$ represent hydrocarbon chains having from 16 to 22 carbon atoms, corresponding in particular to the fatty chains of rapeseed oil, of corn oil, of soya oil, of groundnut oil and of apricot kernel oil, $R_7$ and $R_9$ represent a methylene group, $CH_2$;

n, p and q represent integers such that their sum is between 3 and 30, and preferably equal to 20; or (ii)—$R_6$, $R_8$ and $R_{10}$ represent hydrocarbon chains corresponding to the fatty chains of castor oil;

$R_7$ and $R_9$ represent a methylene radical, $CH_2$;

n, p and q represent integers such that their sum is between 5 and 7.

The concentration of self-emulsifiable oil in the therapeutic composition according to the invention may be approximately between 5 and 700 g/l, preferably approximately between 10 and 500 g/l.

Besides the oily phase and the aqueous phase, the composition according to the invention may contain a conventional immunostimulatory agent such as Avridine®, i.e. N,N-dioctadecyl-N',N'-bis(2-hydroxyethyl) propanediamine, MDP (muramyl dipeptide) derivatives, especially threonyl-MDP, mycolic acid derivatives or Lipid A derivatives.

The therapeutic composition according to the invention may also comprise one or more surface-active agents, in the absence of any oily adjuvant.

The therapeutic composition is then in the form of a micellar solution. This may be prepared by simple mixing of the surface-active agent with a dispersion in water of the antigen or of the in vivo antigen generator.

The surface-active agent may be chosen from the surface-active agents described above, in combination with an oily adjuvant.

Said micellar solution may contain from 0.5 to 500 mg/ml, preferably from 1 to 250 mg/l, of surface-active agent.

A therapeutic composition according to the present invention may comprise an antigen such as a virus, a microorganism, more particularly a bacterium or parasite, or a compound comprising a peptide chain. Such a compound may include a protein or a glycoprotein, especially a protein or glycoprotein obtained from a microorganism, a synthetic peptide or a protein or a peptide obtained by genetic engineering. Said virus and microorganism may be totally inactivated or live and attenuated. By way of virus which may constitute an antigen according to the present invention, there may be mentioned the rabies virus, Aujeszky viruses, influenza viruses, the virus of foot-and-mouth disease or HIV viruses. By way of microorganism of bacterial type which may constitute an antigen according to the present invention, there may be mentioned *E. coli* and those of the genera Pasteurella, Furonculosis, Vibriosis, Staphylococcus and Streptococcus. By way of parasite, there may be mentioned those of the genera Trypanosoma, Plasmodium and Leishmania.

A therapeutic composition according to the invention comprises an antigen concentration which depends upon the nature of this antigen and on the nature of the individual treated. It is, however, particularly noteworthy that an adjuvant according to the invention, which may or may not be combined with an oily adjuvant and/or a surface-active agent as are defined above, makes it possible to decrease in an appreciable manner the usual dose of antigen required. The appropriate antigen concentration may be determined conventionally by those skilled in the art. This dose is generally of the order of 0.1 μg/ml to 1 g/ml, more generally between 1 μg/ml and 100 mg/l.

A therapeutic composition according to the invention may also comprise an in vivo generator of a compound comprising an amino acid sequence, that is to say a biological compound capable of expressing such a compound in the host organism into which said in vivo generator has been introduced. The compound comprising the amino acid sequence may be a protein, a peptide or a glycoprotein.

These in vivo generators are generally obtained by genetic engineering processes.

More particularly, they may comprise living microorganisms, generally a virus, acting as a recombinant vector, into which is inserted a nucleotide sequence, in particular an exogenous gene. Those compounds are known as such and are used in particular as recombinant sub-unit vaccines.

In this regard, reference may be made to the article by M. Eloit et al., Journal of virology (1990) 71, 2925–2431, to International Application WO-A-91.00107 or to International Application WO-A-94/16681.

The microorganism constituting a recombinant sub-unit vaccine is advantageously a non-sheathed recombinant virus chosen, for example, from adenoviruses, the virus of the vaccine, canarypox virus, herpes viruses and baculoviruses. The exogenous gene inserted into the microorganism may, for example, be derived from an Aujeszky virus or HIV.

The in vivo generators according to the invention may also comprise a recombinant plasmid comprising an exogenous nucleotide sequence capable of expressing in a host organism a compound comprising an amino acid sequence. Such recombinant plasmids and their mode of administration into a host organism were described in 1990 by Lin et al., circulation 82:2217,2221; Cox et al., J. of Virol., September 1993, 67, 9, 5664–5667 and in International Application WO/FR 95/00345 dated Mar. 21, 1995, in the name of the Applicant, entitled "Une composition comprenant un plasmide recombinant et ses utilisations comme vaccin et médicament" [A composition comprising a recombinant plasmid and uses thereof as vaccine and medicinal product].

Depending on the nature of the nucleotide sequence comprised within the in vivo generator, the compound comprising the amino acid sequence which is expressed within the host organism may:

(i) be an antigen, and permit triggering of an immune reaction, (ii) have a curative action with respect to a disease, essentially a functional disease, which has been triggered in the host organism. In this case, the in vivo generator allows a therapeutic treatment of the host, of the gene therapy type.

By way of example, such a curative action may comprise the in vivo cytokine generator, such as the interleukins, in particular interleukin 2. The latter permit triggering or reinforcement of an immune reaction aimed at the selective removal of cancer cells.

The concentration of said in vivo generator in the therapeutic composition according to the invention depends, here also, in particular on the nature of said generator and on the host into which it is administered. This concentration may readily be determined by those skilled in the art, on the basis of routine experiment.

As a guide, it may, however, be pointed out that when the in vivo generator is a recombinant microorganism, its concentration in the therapeutic composition according to the invention may be between $10^2$ and $10^{15}$ microorganisms/ml, preferably between $10^5$ and $10^{12}$ microorganisms/ml.

When the in vivo generator is a recombinant plasmid, its concentration in the therapeutic composition according to the invention may be between 0.01 and 100 g/l.

A therapeutic composition according to the invention may be used as a preventive or curative medicinal product. Depending on the nature of the antigen or of the in vivo generator, a therapeutic composition according to the invention may be administered to fish, to crustaceans such as shrimps, to poultry, in particular geese, turkeys, pigeons and chickens, to canines such as dogs, to felines such as cats, to pigs, primates, cattle, sheep and horses. The therapeutic composition according to the invention comprising a pharmaceutically acceptable water-soluble salt as defined above may also be administered to man. The therapeutic composition may be administered in a conventional manner, in particular by subcutaneous, intramuscular or intraperitoneal injection or via the oral or mucosal route.

Another aspect of the invention is use of an adjuvant comprising a pharmaceutically acceptable water-soluble salt as defined above for the preparation of a vaccine intended for the prevention or treatment of an infectious disease, in particular an infectious disease generated by a virus or a microorganism such as those mentioned above.

Another aspect of the invention is the use of a pharmaceutically acceptable water-soluble salt for the preparation of a therapeutic composition intended to treat a functional disease, such as cancer or mucoviscidosis.

In one other of these uses, said pharmaceutically acceptable salt may be combined with at least one of: an oily adjuvant, a surface-active agent and one oily adjuvant which is itself combined with a surface-active agent; these oily adjuvants and surfactants being as defined above.

Adjuvant compositions comprising said pharmaceutically acceptable salt and the oily adjuvant and/or the surfactants mentioned above constitute yet another aspect of the invention. Where appropriate, these adjuvant compositions comprise at least one aqueous phase.

In the latter case, the adjuvant compositions according to the invention, comprising at least one oily phase and, where appropriate, a surfactant, may be in the form of an emulsion. This emulsion may be of the W/O, O/W, W/O/W or microemulsion type.

These emulsions may comprise, by weight, from 0.5% to 99.5% of oily phase per 99.5% to 0.5% of aqueous phase, preferably from 5 to 95% of oily phase per 95 to 5% of aqueous phase and, more preferably, from 25 to 75% of oily phase per 75 to 25% of aqueous phase.

Where appropriate, they may comprise from 0.01 to 500 mg/ml, preferably from 0.1 to 200 mg/ml, of at least one surfactant.

When the adjuvant composition according to the invention comprises, besides the pharmaceutically acceptable salt and an aqueous phase, only one or more surfactants, it is then in the form of a micellar solution. The surfactant content of this micellar solution may be between 0.01 and 900 mg/ml, preferably between 1 and 250 mg/ml.

An adjuvant composition according to the invention usually comprises from 0.02 to 3000 mg/ml, preferably 0.1 to 1000 mg/ml and more preferably from 0.1 to 150 mg/ml, of a pharmaceutically acceptable salt according to the invention.

These compositions are useful for preparing the therapeutic compositions according to the invention.

The latter compositions may then be prepared by simple mixing of the adjuvant composition with a composition comprising an antigen or an in vivo generator of a compound comprising an amino acid sequence.

The invention will be better understood with regard to the examples and figures below.

The examples were performed on OF1 mice whose average weight was between 18 and 20 g.

The results expressed are an average of the results obtained on 10 mice.

The therapeutic compositions comprised Sigma Grade V bovine serum albumin (BSA) as antigen.

The therapeutic compositions were injected subcutaneously.

The humoral immune response was determined by assay of the total IgG and of the total $IgG_1$, according to the ELISA method.

The cell immune response was determined by assay of the $IgG_2a$, according to the ELISA method.

The antibody levels mentioned in the examples correspond to the last dilution above the background noise.

The following abbreviations are used in the examples:

Glu=gluconate

Fruhp=fructoheptonate

Gly=glycerophosphate

Gluhp=glucoheptonate $Al(OH)_3$=aluminum hydroxide

Asp=aspartic acid

Thus, by way of example, GluMn is manganese gluconate.

EXAMPLE 1

Therapeutic compositions (or doses) of 100 µl each, comprising 50 µg of BSA, are prepared.

These therapeutic compositions were injected into the mice on D0 (i.e. the day of injection).

The level of anti-BSA antibodies was determined 14 and 28 days after the injection (primary response).

On D28, the same therapeutic composition was injected into the same mice.

The level of anti-BSA antibodies was determined on D42 and D56.

The results obtained are featured in Table II below.

TABLE II

| Vaccine compositions | Adjuvant | Doses of adjuvant (in mg/dose) | anti-BSA antibody/ primary response (D14) | anti-BSA antibody/ primary response (D28) | anti-BSA antibody/ primary response (D42) | anti-BSA antibody/ primary response (D56) |
|---|---|---|---|---|---|---|
| 1 | — | — | <500 | <500 | <500 | <500 |
| 2 | GluMn | 1 | 64,000 | 32,000 | 256,000 | 256,000 |
| 3 | GluCa | 3 | 16,000 | 8000 | 128,000 | 96,000 |
| 4 | FruhpCa | 1 | 4000 | 2000 | 64,000 | 48,000 |
| 5 | GlyCa | 2 | 4000 | 2000 | 64,000 | 64,000 |
| 6 | GluZn | 0.5 | 16,000 | 6000 | 96,000 | 96,000 |
| 7 | GluhpZn | 1 | 8000 | 6000 | 64,000 | 64,000 |
| Control | — | — | <500 | <500 | <500 | <500 |

The control composition corresponds to mice which were not vaccinated.

The results obtained show that the addition of the adjuvants according to the invention to a therapeutic composition induces a significant immunostimulatory activity as compared with the non-vaccinated control and to the therapeutic compositions not comprising any adjuvants.

It may also be noted that GluMn, although used at a low concentration, allows a particularly high level of antibodies to be obtained.

EXAMPLE 2

The immunostimulatory effect of a water-soluble salt according to the invention, GluMn was compared with that of an insoluble salt, $Al(OH)_3$.

The therapeutic compositions (dose/mouse) used, 100 µl in volume, comprised 50 µg of antigen and 1 mg of $Al(OH)_3$.

Doses not comprising any adjuvants were also injected.

One batch of mice was not vaccinated (control). The results obtained are featured in Table III below.

TABLE III

| Adjuvant | IgG1 primary response D14 | IgG1 primary response D28 | IgG1 secondary response D42 | IgG1 secondary response D56 | IgG2 primary response D14 | IgG2$_a$ primary response D28 | IgG2$_a$ secondary response D42 | IgG2$_a$ secondary response D56 |
|---|---|---|---|---|---|---|---|---|
| — | <500 | <500 | <500 | <500 | <500 | <500 | <500 | <500 |
| GluMn | 32,000 | 64,000 | 256,000 | 256,000 | 4000 | 8000 | 24,000 | 64,000 |
| $Al(OH)_3$ | 16,000 | 64,000 | 128,000 | 256,000 | 1000 | 6000 | 8000 | 32,000 |
| Control | <500 | <500 | <500 | <500 | <500 | <500 | <500 | <500 |

The IgG1s are representative of the humoral response.

The IgG2s are representative of the cell response.

The humoral and cell responses obtained with an adjuvant according to the invention are greater than those obtained with a conventional adjuvant such as $Al(OH)_3$.

EXAMPLE 3

In order to demonstrate the synergy effect between an adjuvant of the water-soluble salt type with an oily adjuvant (Montanide ISA 25 defined in Table I), the effect of various therapeutic compositions was compared. Each of them comprised 50 µg of antigen and had a volume of 100 µl (dose/mouse).

The results obtained are featured in Table IV below:

TABLE IV

| Water-soluble salt | Amount of salt (mg/dose) | Montanide ISA25 (in mg/dose) | Humoral immunity (D14) | Cell immunity (D14) |
|---|---|---|---|---|
| — | — | 25 | 24,000 | 3000 |
| GluMn | 1 | — | 64,000 | 4000 |
| GluMn | 1 | 25 | 96,000 | 8000 |
| GluMn | 0.5 | — | 16,000 | <2000 |
| GluMn | 0.5 | 25 | 96,000 | 6000 |

The combination of an oily adjuvant with a soluble salt according to the invention makes it possible to obtain an antibody level which is superior to that obtained by the simple addition of the antibody levels obtained with each of these adjuvants used individually. Synergy is indeed demonstrated. This synergy is even more pronounced for a low amount (0.5 mg/dose) of GluMn.

EXAMPLE 4

In order to demonstrate the importance of the organic nature of the anion, the immunostimulatory effect of various calcium salts was compared.

Each therapeutic composition, 100 µl in volume, contained 50 µg of antigen and, except for the control, 0.5 mg of a calcium salt, such that the calcium concentration of each composition was 2.7 mg.

The antibodies were assayed 42 days after the vaccination.

Injection of the therapeutic composition was repeated on D28. The antibodies were assayed on D42.

The results obtained are featured in Table V:

TABLE V

| Salts | Humoral response | Cell response |
|---|---|---|
| $CaCO_3$ | 32,000 | 4000 |
| $CaCl_2$ | 64,000 | 24,000 |

TABLE V-continued

| Salts | Humoral response | Cell response |
|---|---|---|
| $CaHPO_4$ | 64,000 | 10,000 |
| GluCa | 128,000 | 32,000 |
| — | 3000 | <2000 |

It was observed during these tests that $CaCl_2$ induced very large lesions.

EXAMPLE 5

A therapeutic composition 100 µl in volume, comprising 50 µg of antigen, was injected into various batches of mice each comprising 5 mice. The local reactions (lesions and granulomae) were evaluated on D8 and D35.

The results obtained are featured in Tables VI and VII respectively.

TABLE VI

| | (D8) | | | | |
|---|---|---|---|---|---|
| Mouse No. Salt concentration (mg/dose) | 1 | 2 | 3 | 4 | 5 |
| GluMn | 1 | + | + | − | − | + |
| GlyMn | 1 | L | + | ++ | + | − |
| GluMn$^+$ | 1 | ++ | +++ | + | − | + |
| GluK | 1 | − | − | − | − | − |
| Asp K and | 1 | − | − | − | − | − |

TABLE VI-continued (D8)

| Mouse No. Salt concentration (mg/dose) | | 1 | 2 | 3 | 4 | 5 |
|---|---|---|---|---|---|---|
| Asp Mg | | | | | | |
| GluCa | 1 | − | − | − | − | − |
| $MnCl^{2+}$ | 1 | +++ | L | L | L | L |
| $Al(OH)_3$ | 1 | +++ | +++ | ++ | +++ | ++++ |

TABLE VII (D35)

| Mouse No. Salt concentration (mg/dose) | | 1 | 2 | 3 | 4 | 5 |
|---|---|---|---|---|---|---|
| GluMn | 1 | − | + | + | + | − |
| GlyMn | 1 | − | + | + | + | + |
| GluMn+ | 1 | ++ | ++ | ++ | +++ | + |
| GluK | 1 | − | − | − | − | − |
| Asp K and Asp Mg | | | | | | |
| GluCa | 1 | − | − | − | − | − |
| $MnCl^{2+}$ | 1 | +++ | LL | LL | L | L |
| $Al(OH)_3$ | 1 | +++ + | +++ | ++ | +++ | ++++ |

(*): GluMn combined with 25 mg of MONTANIDE ISA 25
− = no granuloma
+ = small granuloma
++ = medium granuloma
+++ = large granuloma
++++ = very large granuloma
− = no lesions
L = small lesion
LL = medium lesion
LLL = large lesion
LLLL = very large lesion
DCD = mice that died during the experiment The chosen concentration of $Al(OH)_3$ corresponds to the concentration at which this salt allows the largest immune response to be obtained. This concentration of $Al(OH)_3$ is that used in the above examples.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What is claimed is:

1. An immunogenic composition in an emulsion form comprising at least one aqueous phase and at least one oily phase, said composition comprising (i) at least one antigen or at least one in vivo generator of a compound comprising an amino acid sequence and (ii) at least one adjuvant comprising manganese gluconate, calcium gluconate, zinc gluconate, calcium fructoheptonate, zinc glucoheptonate, or calcium glycerophosphate and (iii) an oily phase adjuvant which is a self-emulsifiable oil comprising an ester of ethoxylated fatty acids corresponding to one of the following formulae:

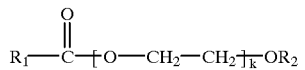
(II)

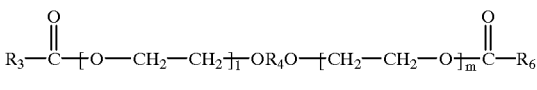
(III)

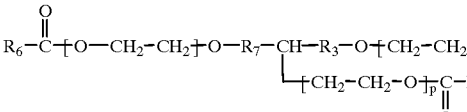
(IV)

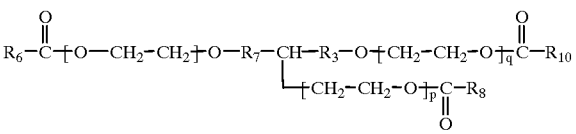

in which $R_1$, $R_3$, $R_5$, $R_6$, $R_8$ and $R_{10}$ represent a saturated or unsaturated, linear or branched hydrocarbon chain having from 5 to 30 carbon atoms;

$R_2$, $R_4$, $R_7$ and $R_9$ represent a saturated or unsaturated, linear or branched hydrocarbon chain having from 1 to 5 carbon atoms;

the total number of ethylene oxide molecules represented in the above-mentioned formulae II, III and IV by k, l+m and n+p+q, respectively, being an integer such that said compounds have a hydrophobic/lipophilic (HLB) value between about 4 and about 10, said adjuvant being present in an amount effective to increase the immune response.

2. The immunogenic composition of claim 1, wherein the pharmaceutically acceptable salt is manganese gluconate.

3. The immunogenic composition of claim 1, wherein the emulsion is of the W/O/W, O/W or microemulsion type.

4. The immunogenic composition of claim 1, wherein said oily phase including the adjuvant further comprises a surface-active agent.

5. The immunogenic composition of claim 4, wherein said surface-active agent comprises (i) an ester obtained by condensation of a fatty acid with a sugar, a poly-ethylene glycol, sorbitol, glycerol, or a derivative of such an ester whose hydrophilicity has been modified, and (ii) an ethoxylated plant oil.

6. The immunogenic composition of claim 1, wherein said HLB value is between about 5 and about 9.

7. The immunogenic composition of claim 1, further comprising a surface-active agent, said composition being in a micellar solution form.

8. The immunogenic composition of claim 7, wherein the surface-active agent is (i) an ester obtained by condensation of a fatty acid with a sugar or glycerol, or a derivative of such an ester obtained by grafting hydrophilic functions such as alcohol, polyol, ethylene oxide, propylene oxide, carboxylic acid, amine or amide, or (ii) an ethoxylated plant oil.

* * * * *